United States Patent [19]

Phillips

[11] 4,201,226
[45] May 6, 1980

[54] COMBINATION INSTRUMENT FOR TAKING BIOMECHANICAL MEASUREMENTS

[76] Inventor: Robert L. Phillips, 900 Eighth Ave. S., Great Falls, Mont. 59405

[21] Appl. No.: 819,003

[22] Filed: Jul. 26, 1977

[51] Int. Cl.² ............................................. A61B 5/10
[52] U.S. Cl. ................................... 128/774; 128/779; 33/143 C; 33/143 J; 33/174 D
[58] Field of Search ............... 128/2 S, 2 R, 779, 774, 128/782; 33/143 C, 143 J, 143 M, 143 K, 174 D, 111, 3 A, 3 B, 3 C

[56] References Cited

U.S. PATENT DOCUMENTS

| | | | |
|---|---|---|---|
| 1,039,901 | 10/1912 | Constantinescu | 33/143 K X |
| 1,488,435 | 3/1924 | Pickens | 33/111 |
| 2,589,904 | 3/1952 | Vladeff | 33/143 M X |
| 3,196,551 | 7/1965 | Provost et al. | 128/2 S |
| 3,358,373 | 12/1967 | Martin | 128/2 S X |
| 4,033,329 | 7/1977 | Gregory et al. | 128/2 S |
| 4,037,480 | 7/1977 | Wagner | 128/2 S |

FOREIGN PATENT DOCUMENTS

| | | | |
|---|---|---|---|
| 92010 | 4/1938 | Belgium | 33/143 M |
| 660168 | 5/1938 | Fed. Rep. of Germany | 33/3 A |
| 1531671 | 7/1968 | France | 128/2 S |
| 360914 | 11/1931 | United Kingdom | 33/3 C |
| 310648 | 9/1971 | U.S.S.R. | 128/2 S |

*Primary Examiner*—Lee S. Cohen
*Attorney, Agent, or Firm*—Mallinckrodt & Mallinckrodt

[57] ABSTRACT

A combination instrument, for use in making biomechanical measurements of the limbs, joints, and appendages of a human body, comprises a scaled straightedge adapted to slidably receive thereon a set of mutually cooperative caliper arms which, themselves, slidably carry body-contacting pads for adjustable placement relative to each other longitudinally of the caliper arms and relative to body irregularities, one of which arms carries a gravity meter for indicating angle measurements, the straightedge being further adapted to pivotally receive at one end thereof a protractor device for rotational movement relative to the straightedge and the caliper arms.

4 Claims, 8 Drawing Figures

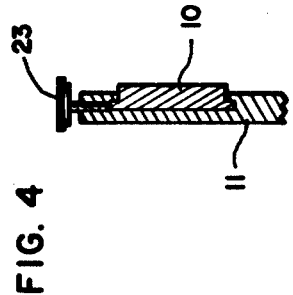
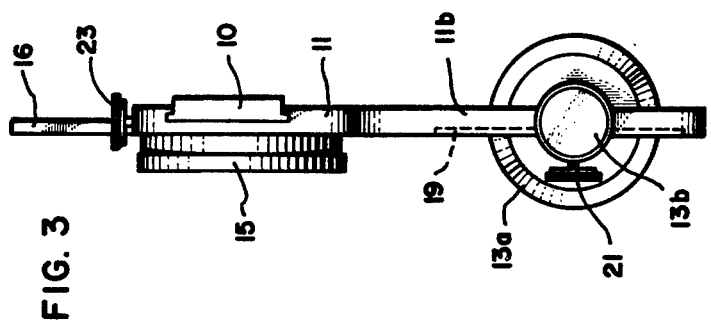
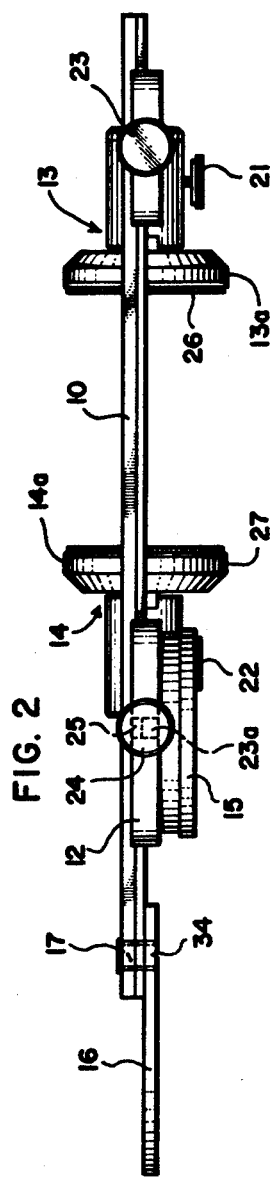
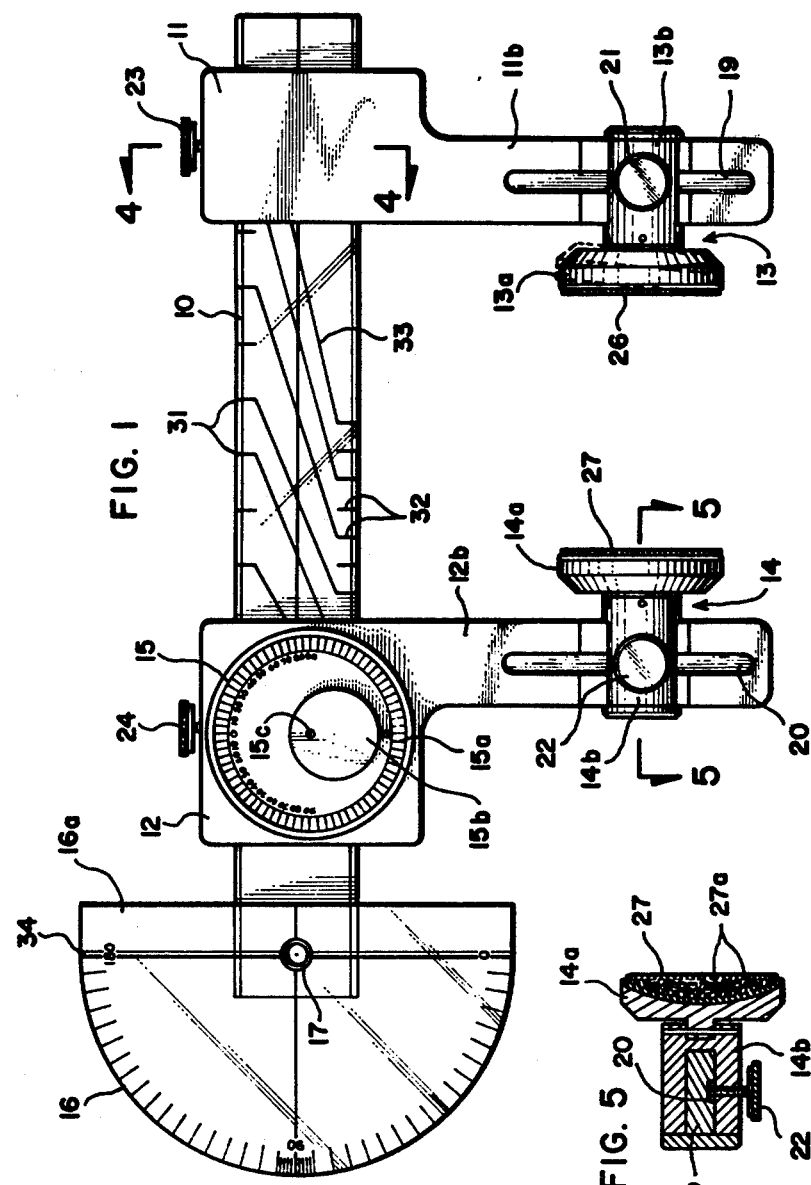
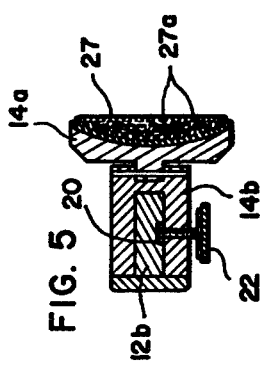

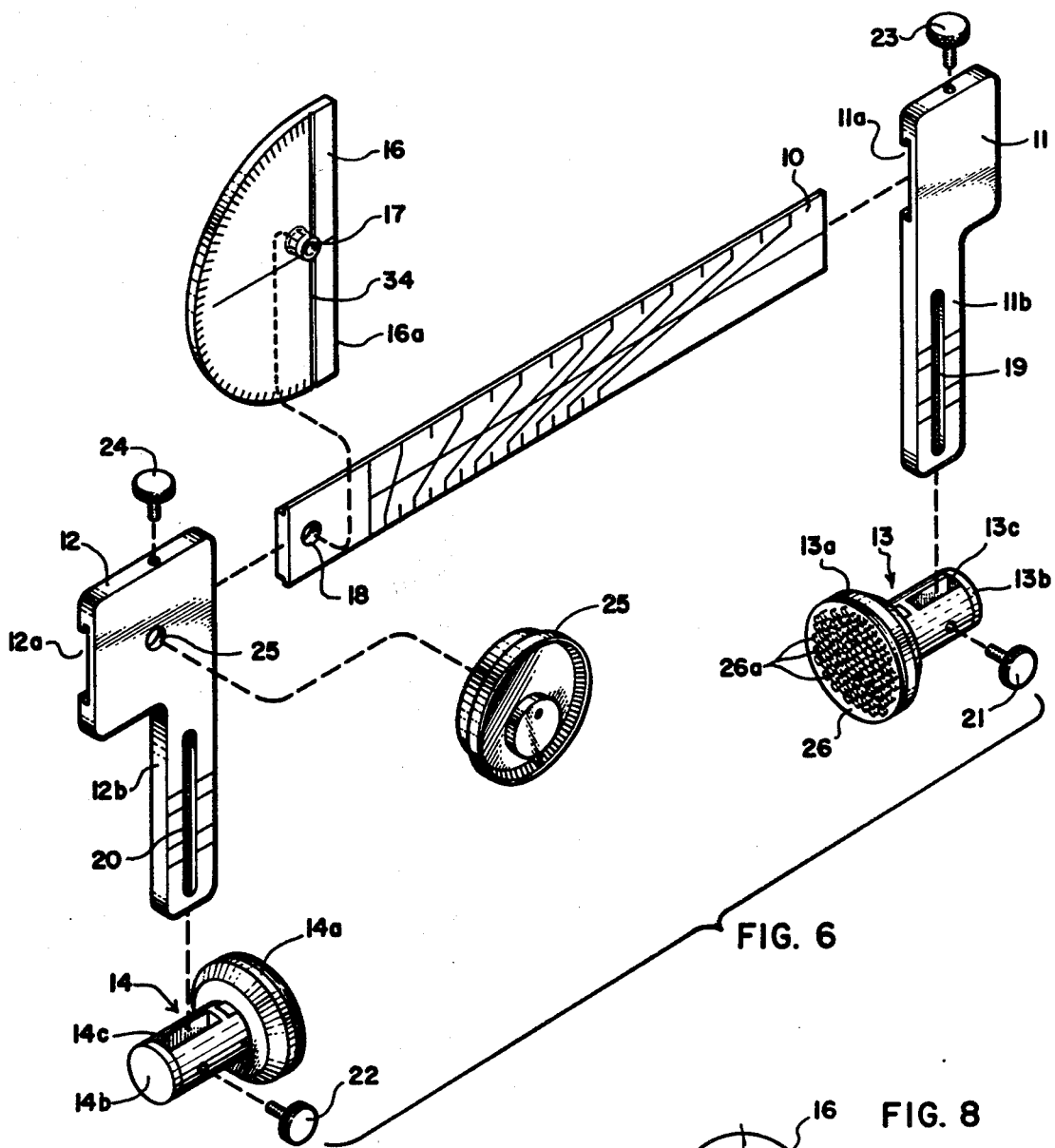
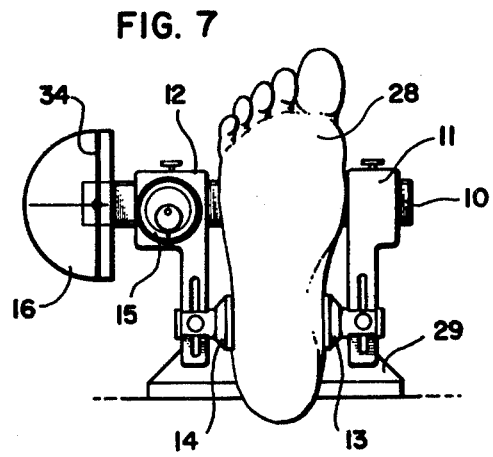
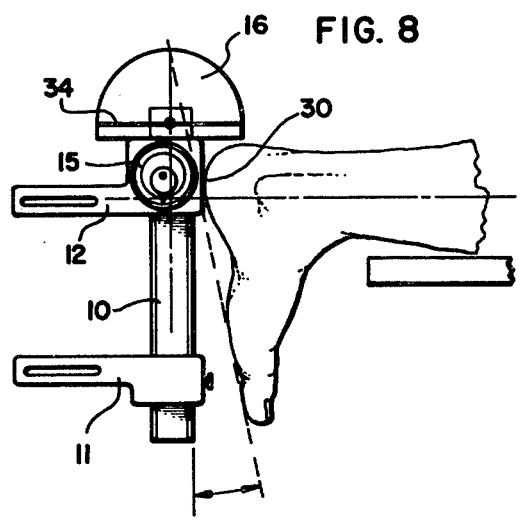

COMBINATION INSTRUMENT FOR TAKING BIOMECHANICAL MEASUREMENTS

BACKGROUND OF THE INVENTION

1. Field

The invention is in the field of measuring instruments for use in making various measurements involving the limbs, joints, and appendages of the human body.

2. State of the Art

For many years, medical doctors and other persons concerned with the human body and activities thereof have used various instruments, such as calipers, protractors, and rulers, for taking biomechanical measurements. Such instruments have been developed and used for a variety of special purposes, but generally speaking the measurements taken have varied widely even among doctors skilled in the field. For the most part, measurements of the same conditions taken by different people have not been consistent.

Moreover, none of these instruments have provided for quickly, easily, and accurately obtaining all the information required to determine what corrective measures should be applied in instances of athletes having some physical condition that could lead to injuries if not corrected.

SUMMARY OF THE INVENTION

In accordance with the invention, an instrument is provided for enabling a medical doctor, an athletic coach, or even an unskilled person to spot abnormal conditions involving limbs, joints, and/or appendages, such as the feet, which could lead to injuries during participation in sports if not corrected.

For example, a physical condition in athletes which makes them prone to the so-called "shin splint syndrome" has been ascertained by comparing measurements of the ranges of inversion and eversion of the subtalar joint; dorsiflexion of the ankle, with the knee both flexed and extended; the frontal plane position of the tibia, subtalar joint static; and the position of the calcaneus in relation to the floor, subtalar joint static, of those athletes known to have suffered from such shin splint syndrome with similar measurements made on those athletes who would be subjected to play commonly resulting in the shin splint syndrome.

For making the required measurements, the instrument of the invention comprises several interrelated instruments that can be used individually as well as in concert. Thus, a scaled straightedge is adapted to slidably receive a set of mutually cooperative caliper arms, which, themselves, are adapted to slidably receive, for movement longitudinally thereof and for adjustment relative to body irregularities, a pair of body-contacting pads. One of the caliper arms also carries a gravity meter for indicating angle measurements. The straightedge is further adapted to pivotally receive, at one end thereof, a protractor device for rotational movement relative to the straightedge and caliper arms.

THE DRAWINGS

An embodiment presently contemplated as the best mode of carrying out the invention in practice is illustrated in the accompanying drawings, in which:

FIG. 1 is a view in front elevation of the instrument in its combinational form ready for the taking of certain measurements involving the combined functions of the several component parts, adjustability of the body-contacting pads thereof relative to the body being indicated by dotted lines;

FIG. 2, a top plan view;

FIG. 3, an end elevation looking from the right in FIG. 1;

FIG. 4, a fragmentary vertical section taken on the line 4—4 of FIG. 1;

FIG. 5, a horizontal section taken on the line 5—5 of FIG. 1;

FIG. 6, an exploded view showing pictorially the several parts of the instrument of the foregoing figures;

FIG. 7, a view corresponding to that of FIG. 1, but showing the instrument being used to take one type of measurement with respect to a persons foot, the view being drawn to a reduced scale; and FIG. 8, a similar view of the instrument in use for taking a different measurement on a persons foot, the body-contacting pads having been removed as nonessential in the taking of the particular measurement concerned.

DETAILED DESCRIPTION OF THE ILLUSTRATED EMBODIMENT

In the specific form illustrated, the instrument of the invention comprises a scaled straightedge 10 having slidably mounted thereon a set of mutually cooperative caliper arms 11 and 12 for relative movement longitudinally of the straightedge 10.

Each of the caliper arms 11 and 12 slidably carry thereon respective body-contacting pads 13 and 14, and the caliper arm 12 carries a gravity meter 15 for indicating angle measurements.

A protractor 16 is removably pivoted at one end of straightedge 10, as by means of a stub shaft 17 fitted into a receiving opening 18, FIG. 6, in the straightedge.

As illustrated, the caliper arms 11 and 12 are provided with transverse, straightedge-receiving slideways 11a and 12a, respectively, FIG. 6, adjacent to one set of corresponding ends thereof and with elongate members 11b and 12b, respectively, extending therefrom and substantially normal thereto for slidably receiving body-contacting pads 13 and 14, respectively. Such pads 13 and 14 have respective pad members 13a and 14a articulatively (see dotted line position of pad member 13a, FIG. 1) carried by respective stubby stem members 13b and 14b, each providing a slideway, 13c and 14c, for receiving the corresponding elongate member 11b or 12b. Such elongate members are advantageously provided with slideway grooves 19 and 20, respectively, longitudinally thereof for accommodating the protruding ends of respective set screws 21 and 22 during sliding movement of body-contacting pads 13 and 14 along the respective elongate members and for aiding securement of such pads 13 and 14 at selected positions along such elongate members by means of the set screws.

Articulative attachment of pad members 13a and 14a to their respective stem members 13b and 14b, as indicated in FIG. 1 and shown in detail in FIG. 5, is important to enable such pad members to accommodate themselves to body irregularities.

Set screws 23 and 24 serve to secure caliper arms 11 and 12, respectively, in adjusted positions along the length of straightedge 10.

As previously mentioned, one of the caliper arms (as here shown the caliper arm 12) carries gravity meter 15, which may be permanently affixed to the arm or which may be removably attached thereto, as by means of a stub shaft 23a, FIG. 2, which frictionally fits into a receiving opening 25 in the arm. Gravity meter 15 indicates angle measurements on its scale 15a, FIG. 1, when its pivotally-mounted, pointer-provided disk member 15b swings to one side or another on its eccentric pivot mounting 15c.

For taking other angle measurements relative to the position of straightedge 10 assumed by it in carrying out a given measuring operation, protractor 16 is swung to an appropriate position on its pivot mounting 17 at one end of the straightedge.

Both for the sake of accuracy in taking various body measurements and for making the measurement operation more comfortable for the person subjected to the taking of measurements, pad members 13a and 14a are of concave formation, as indicated in FIG. 5, and are preferably lined with elastomer disks 26 and 27, respectively, which advantageously include numerous protruding fingers, see 27a, throughout to provide a non-skid surface for guarding against slippage once the instrument is placed and set in measurement position. A diameter of approximately one and one-half inches is a suitable size for the concave disks 13a and 14a and for the elastomer liner disks 26 and 27.

As previously indicated, a variety of body measurements can be effectively taken, using the instrument of the invention, by even unskilled persons. Thus, a medical doctor can provide instructions as to the type of measurements to be taken and how the instrument is to be applied, and an athletic coach or some other person even less skilled can take accurate measurements which will be consistent when repeatedly carried out.

By way of example, one type of measurement for determining the position of the malleoli, with the subtalar joint neutral, is illustrated in FIG. 7, the protractor 16 remaining idle in this instance. It can be seen that body-contacting pads 13 and 14 hold the instrument securely and comfortably in adjusted position on a foot 28 of the person undergoing measurement. As illustrated, it is desirable that the leg of the person rest firmly on and along a supporting surface 29 during the measuring operation.

Again, for example, as illustrated in FIG. 8, the instrument may be used to determine dorsiflexion of the ankle with the knee extended. As shown, the instrument is held against the heel 30 of the foot of the person subjected to the measurement operation, with the straightedge 10 held vertically, as accurately determined by the position of the pointer of gravity meter 15, protractor 16 being employed as shown. Here, the body-contacting pads 13 and 14 have been removed from caliper arms 11 and 12 for convenience, since the caliper is not needed for this measurement operation. When the foot is flexed forwardly, as shown, and when straightedge 10 is similarly swiveled forwardly relative to protractor 16, which is held in the position shown, the angle indicated is measured by meter 15. Other uses for the protractor in the combination will be apparent to skilled podiatrists.

It will be apparent that a great variety of body measurements can be made in accordance with the invention, using the versatile facilities of the instrument of the invention employing various or all of the component parts of the instrument as the particular measurement operation may require.

The scale marked on the straightedge may be of any type required for particular uses. As illustrated, there is a top scale 31 and a bottom scale 32 carrying twice as many gradations as the top scale. Both are conveniently divided into fractions of an inch, all or alternate of the gradation in the top scale 31 being connected by diagonal lines 33 with corresponding gradations on the bottom scale; thus, for example, the first to the first, third to the third, fifth to the fifth, etc., as indicated. This is useful for bisecting the heel, since the absolute center is required for certain podiatric purposes.

It is desirable that a groove 34 be made in the surface of protractor 16 parallel with the straightedge 16a of such protractor and substantially a quarter of an inch therefrom as illustrated to facilitate certain measurements.

Whereas this invention is here illustrated with respect to a particular embodiment thereof presently contemplated as the best mode of carrying out the invention in practice, it should be understood that various changes may be made within the generic teachings herein.

I claim:

1. A combination measuring instrument for use in the taking of various biomechanical measurements, comprising a scaled straightedge; a set of elongate, mutually cooperative, caliper arms slidably attached to the straightedge for relative movement therealong and including means for rigidly fixing said arms in adjusted positions relative to each other and to the straightedge; a set of body-contacting pads having stub stem members, respectively, slidably attached to respective caliper arms, for movement longitudinally therealong, and having body-contacting pad members pivotally attached to the respective stem members so as to accommodate body irregularities; means for fixedly securing said pads to said arms in adjusted relative positions; and a gravity meter attached to one of said caliper arms.

2. A combination instrument in accordance with claim 1, wherein the instrument further comprises a protractor pivotally secured to the straightedge at one end thereof.

3. A combination instrument in accordance with claim 2, wherein there is a marking along the protractor parallel with the straightedge of said protractor and spaced backwardly therefrom approximately one-quarter of an inch.

4. A combination instrument in accordance with claim 3, wherein the marking is a groove cut into a face of the protractor.

* * * * *